United States Patent [19]

Wuelknitz et al.

[11] Patent Number: 5,292,500
[45] Date of Patent: Mar. 8, 1994

[54] PLAQUE-INHIBITING TOOTHPASTE COMPRISING ANTIBACTERIAL BIGUANIDES

[75] Inventors: Peter Wuelknitz, Langenfeld-Berghausen; Rudolf Lehmann, Leichlingen; Walter Ploeger, Hilden; Franz Foerg, Langenfeld, all of Fed. Rep. of Germany

[73] Assignee: Henkel Kommanditgesellschaft auf Aktien, Duesseldorf, Fed. Rep. of Germany

[21] Appl. No.: 835,920

[22] PCT Filed: Aug. 16, 1990

[86] PCT No.: PCT/EP90/01346

§ 371 Date: Feb. 25, 1992

§ 102(e) Date: Feb. 25, 1992

[87] PCT Pub. No.: WO91/02513

PCT Pub. Date: Mar. 7, 1991

[30] Foreign Application Priority Data

Aug. 25, 1989 [DE] Fed. Rep. of Germany ....... 3928063

[51] Int. Cl.$^5$ .............................................. A61K 7/22
[52] U.S. Cl. .......................................... 424/49; 424/53
[58] Field of Search ................................. 424/49, 53

[56] References Cited

U.S. PATENT DOCUMENTS

| | | | |
|---|---|---|---|
| 2,684,924 | 7/1954 | Rose et al. | 167/30 |
| 2,990,425 | 6/1961 | Senior | 260/301 |
| 3,468,898 | 9/1969 | Cutler et al. | 260/301 |
| 3,547,828 | 12/1970 | Mansfield et al. | 252/351 |
| 3,707,535 | 12/1972 | Lew | 260/210 |
| 3,839,318 | 10/1974 | Mansfield | 260/210 R |
| 4,022,834 | 5/1977 | Gundersen | 260/564 |
| 4,053,636 | 10/1977 | Eustis, III et al. | 424/326 |
| 4,198,392 | 4/1980 | Juneja | 424/48 |
| 4,495,170 | 1/1985 | Beyts et al. | 424/49 |
| 4,748,158 | 5/1988 | Biermann et al. | 514/49 |
| 4,923,685 | 5/1990 | Wülknitz et al. | 424/54 |
| 5,145,665 | 9/1992 | Klueppel et al. | 424/49 |

FOREIGN PATENT DOCUMENTS

| | | |
|---|---|---|
| 0026252 | 4/1981 | European Pat. Off. |
| 0077167 | 4/1983 | European Pat. Off. |
| 0304627 | 3/1989 | European Pat. Off. |
| 1943689 | 3/1970 | Fed. Rep. of Germany |
| 2036472 | 2/1971 | Fed. Rep. of Germany |
| 2126539 | 12/1971 | Fed. Rep. of Germany |
| 2158149 | 6/1972 | Fed. Rep. of Germany |
| 3001064 | 7/1981 | Fed. Rep. of Germany |
| 3444958 | 6/1986 | Fed. Rep. of Germany |
| 0702268 | 1/1954 | United Kingdom |
| 0705838 | 3/1954 | United Kingdom |

OTHER PUBLICATIONS

Ullmann, Encyklopaedie der technischen Chemie, 4th ed., vol. 7, 1974, p. 298.
"Poliertonarden (Polishing Aluminas)", Giulini Chemie.
Culminal MHPC, Granulat, 1982.

*Primary Examiner*—Ronald W. Griffin
*Attorney, Agent, or Firm*—Wayne C. Jaeschke; Norvell E. Wisdom, Jr.; John D. Wood

[57] ABSTRACT

Toothpastes containing 10 to 60% by weight of a polishing agent, 2 to 20% by weight of a humectant, 0.5 to 5% by weight water-soluble consistency regulators, 0.02 to 0.5% by weight antibacterial biguanides and 1 to 5% by weight other additives from the group consisting of surfactants, flavoring oils and sweeteners show particularly high biguanide availability if they contain predominantly α-aluminium oxide trihydrate as the polishing agent, nonionic polysaccharide derivatives as the consistency regulators, an alkyl glycoside and, optionally, a nonionic solubilizer for the flavoring oil as surfactants and L-aspartyl-L-phenyl alanine methyl ester as sweetener.

16 Claims, No Drawings

PLAQUE-INHIBITING TOOTHPASTE COMPRISING ANTIBACTERIAL BIGUANIDES

BACKGROUND OF THE INVENTION

Field of the Invention

This invention relates to a toothpaste in the form of a dispersion of water-insoluble polishing agents in an aqueous carrier which contains an antimicrobial biguanide compound as plaque-inhibiting component and of which the other components are selected in regard to type and quantity so that optimal inhibition of plaque formation is obtained despite a relatively low dosage of the antimicrobial biguanide compounds.

Statement of Related Art

It has long been known that antimicrobial biguanide compounds are effective in inhibiting the formation of plaque. However, their effect in this regard is greatly reduced or totally eliminated by many components typically present in toothpastes, more particularly by certain polishing agents, by many binders or consistency regulators, surfactants and even by sweeteners.

Accordingly, there has been no shortage of attempts to find components which do not impair the effect of the antimicrobial biguanides. Thus, according to DE-OS 21 58 149 for example, $\alpha$-aluminium oxide trihydrate in a certain particle size is used as polishing agent. On the other hand, according to DE-OS 34 44 958, certain surfactants can enhance the effect of an antimicrobial biguanide. It has now been found that even this effect is greatly reduced by certain toothpaste components, for example by anionic binders or consistency regulators, anionic sweeteners and certain solubilizers which are necessary for solubilizing any flavoring oils present. A toothpaste which combines high biguanide availability with a satisfactory plaque-inhibiting effect, even despite a low dosage of the antimicrobial biguanide compounds is not mentioned in the prior art. The object of the present invention was to provide such a toothpaste.

SUMMARY OF THE INVENTION

The present invention relates to a toothpaste in the form of a dispersion containing
- 10 to 60% by weight polishing agents,
- 2 to 20% by weight humectants,
- 0.5 to 50% by weight water-soluble consistency regulators,
- 0.02 to 0.5% by weight antimicrobial biguanides,
- 1 to 5% by weight other additives from the group consisting of surfactants, flavoring oils and sweeteners, characterized in that it contains
- predominantly $\alpha$-aluminium oxide trihydrate as polishing agent,
- nonionic polysaccharide derivatives as consistency regulators,
- an alkyl glycoside and optionally a nonionic solubilizer for the flavouring oil as surfactants and
- L-aspartyl-L-phenyl alanine methyl ester as sweetener.

DESCRIPTION OF PREFERRED EMBODIMENTS $\alpha$-Aluminum oxide trihydrate, $Al(OH)_3$, is a known polishing agent for toothpastes. A ground quality in which the particles are predominantly (at least 98%) smaller than $50\mu$ in size with an average of approximately 1 to $10\mu$ is particularly suitable.

The toothpaste according to the invention preferably contains a mixture of $\alpha$-aluminium oxide trihydrate (A) and a weakly calcined alumina (B) in a ratio by weight of A to B of 100 : (1-15) in a quantity of 30 to 604 by weight, because a particlularly good polishing effect with no roughening secondary effect is obtained in this way.

The weakly calcined alumina preferably has a gamma-aluminium oxide ($\gamma$-$Al_2O_3$) content of approximately 20% by weight and an alpha-aluminium oxide ($\alpha$-$Al_2O_3$) content of approximately 80% by weight, an agglomerate size below $20\mu$, an average primary crystal size of 0.5 to $1.5\mu$ and an apparent density of 500 to 600 g/l.

Suitable weakly calcined aluminas are obtained by calcination from aluminium hydroxide. Aluminium hydroxide is converted by calcination into $\alpha$-$Al_2O_3$ which is thermodynamically stable at temperatures above 1,200° C. The thermodynamically unstable forms of $Al_2O_3$ occurring at temperatures between 400° and 1,000° C. are known as gamma forms (cf. Ullmann, Encyclopadie der technischen Chemie, 4th Edition (1974), Vol. 7, page 298). The degree of calcination, i.e. the conversion into the thermodynamically stable $\alpha$-$Al_2O_3$, can be adjusted as required through the calcination temperature and the calcination time. An alumina having an $\gamma$-$Al_2O_3$ content which is lower, the higher the calcination temperature and the longer the calcination time, is obtained by weak calcination. Weakly calcined aluminas are distinguished from pure $\alpha$-$Al_2O_3$ by lower agglomerate hardness, a larger specific surface and larger pore volumes.

Aluminium oxide polishes are commercially available in various degrees of calcination, fineness and apparent density, as for example the "Poliertonerden (Polishing Aluminas)" of Giulini Chemie.

The humectants used include glycerol, sorbitol, propylene glycol and polyethylene glycols; glycerol and/or sorbitol are preferred.

Suitable water-soluble consistency regulators are the nonionic polysaccharide derivatives, for example methyl, hydroxyethyl and hydroxypropyl ethers, of cellulose, starch, guar and vegetable gums. Hydroxyethyl cellulose and methyl hydroxypropyl cellulose are preferably used.

The 1,1'-hexamethylene bis- [5- (4-chlorophenyl)-biguanide] ("chlorhexidine") known from GB-A-705,838 in the form of a water-soluble, physiologically compatible salt, for example in the form of the acetate or gluconate, is preferably used as the antimicrobial biguanide compound. Other antimicrobial biguanide compounds suitable for use in accordance with the invention are, for example, 1,1'-hexamethylene bis-[5-(4-fluorophenyl)-biguanide] (fluorhexidine) the polyhexamethylene biguanide compounds of the Vantocil ® IB (ICI) type known from GB-A-702,268 and also the antimicrobial biguanide compounds known from U.S. Pat. Nos. 2,684,924, 2,990,425, 3,468,898, 4,022,834, 4,053,636 and 4,198,392.

Nonionic surfactants of the alkyl glycoside type are used as surfactants in the toothpastes according to the invention. Alkyl glycosides,, their production and their use as surfactants are known, for example, from U.S. Pat. Nos. 3,839,318, 3,707,535, 3,547,828, DE-A-19 43 6891 DE-A-20 36 472 and DE-A-30 01 064 and from EP-A-77 167. They are prepared in particular by reaction of glucose or oligosaccharides with primary $C_{8-16}$ alcohols. So far as the glycoside residue is concerned, both monoglycosides in which a cyclic sugar residue is attached to the fatty alcohol by a glycoside bond and oligomeric glycosides having a degree of oligomerization (OG) of preferably up to 3 are suitable. Preferred alkyl glycosides for the production of the preparations according to the invention are those containing 8° to 18° C. atoms in the alkyl group and having an average degree of oligomerization of the glycoside residue of 1 to 3. The degree of oligomerization (OG) is a statistical mean value based on a homolog distribution typical of such industrial products. The alkyl glycosides are preferably present in the toothpaste according to the invention in quantities of 0.025 to 2.5% by weight.

The organoleptic properties of the toothpaste according to the invention can be improved by the addition of flavoring oils and sweeteners. Suitable flavoring oils are any of the natural and synthetic flavors typically used in oral and dental hygiene preparations. Natural flavors may be used both in the form of essential oils isolated from the drugs and in the form of the individual components isolated from the essential oils. The toothpaste should preferably contain at least one flavoring oil from the group consisting of peppermint oil, spearmint oil, anise oil, Japanese anise oil, caraway oil, eucalyptus oil, fennel oil, cinnamon oil, clove oil, geranium oil, sage oil, pimento oil, thyme oil, marjoram oil, basil oil, lemon oil, wintergreen oil or one or more synthetic components of these oils isolated therefrom. The most important components of the oils mentioned are, for example, menthol, carvone, anethol, cineol, eugenol, cinnamaldehyde, caryophyllene, geraniol, citronellol, linalool, salvene, thymol, terpinene, terpineol, methyl chavicol and methyl salicylate. Other suitable flavors are, for example, menthyl acetate, vanillin, ionone, linalyl acetate, rhodinol and piperitone.

According to the invention, a nonionic solubilizer is necessary for solubilizing these mostly water-insoluble flavoring oils. The solubilizers in question belong to the group of surface-active compounds. Accordingly, the present invention also relates to a toothpaste according to the invention containing 0.1 to 0.5% by weight of a flavoring oil and 0.1 to 0.7% by weight of a nonionic solubilizer, preferably from the group consisting of ethoxylated fatty acid glycerides, ethoxylated fatty acid sorbitan partial esters or fatty acid partial esters of glycerol or sorbitan ethoxylates. Solubilizers from the group of ethoxylated fatty acid glycerides comprise above all adducts of 20 to 60 mol ethylene oxide with mono- and diglycerides of linear $C_{12-18}$ fatty acids or with triglycerides of hydroxyfatty acids, such as hydroxystearic acid or ricinoleic acid. Other suitable solubilizers are ethoxylated fatty acid sorbitan partial esters, i.e. preferably adducts of 20 to 60 mol ethylene oxide with sorbitan monoesters and sorbitan diesters of $C_{12-18}$ fatty acids. Fatty acid partial esters of glycerol or sorbitan ethoxylates, i.e. preferably mono- and diesters of $C_{12-18}$ fatty acids and adducts of 20 to 60 mol ethylene oxide with 1 mol glycerol or with 1 mol sorbitol, are also suitable solubilizers.

The toothpaste according to the invention preferably contains adducts of 20 to 60 mol ethylene oxide with hydrogenated or non-hydrogenated castor oil (i.e. with hydroxystearic acid or ricinoleic acid triglyceride), with glycerol mono- and/or distearate or with sorbitan mono- and/or distearate as solubilizers for any flavoring oils present.

Suitable sweeteners are either natural sugars, for example sucrose, maltose, lactose and fructose, or synthetic sweeteners, but preferably nonionic or amphoteric substances. L-Aspartyl-L-phenyl alanine methyl ester, commercially available under the name of Aspartame ® is particularly suitable as the sweetener.

Other known toothpaste additives may also be added in small quantities of, in all, up to at most 3% by weight, providing they are compatible with the antimicrobial biguanide and do not impair its effect. Such additives are, for example, caries-inhibiting agents, such as sodium fluoride or sodium monofluorophosphate, pigments, for example titanium dioxide, dyes, pH regulators for adjusting a pH value of preferably 6 to 8 and buffers, for example citric acid and salts thereof or phosphoric acid and alkali salts thereof, wound-healing and anti-inflammatory agents, such as for example allantoin, urea, azulene and active substances from camomile.

The following Examples are intended to illustrate the invention without limiting it in any way.

EXAMPLES

| (Composition in % by weight) | Toothpaste | | | | |
|---|---|---|---|---|---|
| | 1 | 2 | 3 | 4 | 5 |
| Aluminium oxide trihydrate[1] | 45.0 | 45.0 | 35.0 | 35.0 | 54.0 |
| Alumina, weakly calcined[2] | — | 1.0 | — | 1.0 | 1.0 |
| Glycerol | 10.0 | 10.0 | 15.0 | 15.0 | 5.0 |
| Sorbitol (70%) | — | — | — | — | 5.0 |
| Hydroxyethyl cellulose[3] | 1.5 | 1.5 | 1.5 | 1.5 | — |
| Methyl hydroxypropyl celluse[4] | 1.5 | 1.5 | 1.5 | 1.5 | — |
| Chlorhexidine digluconate | 0.3 | 0.3 | 0.2 | 0.2 | 0.2 |
| $C_{12-14}$ alkyl glucoside (OG - 1.3) | 0.25 | 0.25 | 0.25 | 0.25 | 0.5 |
| HR 60[5] | 0.4 | 0.4 | 0.1 | 0.1 | 0.2 |
| Peppermint oil | 0.4 | 0.4 | 0.1 | 0.1 | 0.2 |
| Aspartame ® | 0.2 | 0.2 | 0.1 | 0.1 | 0.1 |
| Water | ad 100 | ad 100 | ad 100 | ad 100 | ad 100 |

[1] Hydrated Alumina, Grade C 333, of ALCOA, Chem. Div. was used.
[2] The commercial product Poliertonerde ("Polishing Alumina") was used
[3] The commercial product Cellobond HEC 400 T of BP was used
[4] The commercial product Culminal MHPC 100 of Henkel was used
[5] Adduct of 60 mol ethylene oxide with hydrogenated castor oil

What is claimed is:

1. A toothpaste in the form of an aqueous dispersion comprising:

10 to 60% by weight polishing agents, 2 to 20% by weight humectants 0.5 to 5% by weight of water-soluble consistency regulators, 0.02 to 0.5% by weight of antimicrobial biguanides selected from the group consisting of water-soluble, physiologically compatible salts of chlorhexidine, 1 to 5% by weight of other additives from the group consisting of surfactants, flavoring oils, and sweeteners, wherein the improvement comprises the presence in the toothpaste of:

predominantly α-aluminium oxide trihydrate, said α-aluminum oxide trihydrate having particles predominantly smaller than 50 micrometers in size with an average of approximately 1 to 50 micrometers, as polishing agent, nonionic polysaccharide derivatives as consistency regulators, an alkyl glycoside and, optionally, a nonionic solubilizer for the flavouring oil as surfactants, and L-aspartyl-L-phenyl alanine methyl ester as sweetener.

2. A toothpaste as claimed in claim 1, which contains from 30 to 60% by weight of a mixture of α-aluminium oxide trihydrate (A) and a weakly calcined alumina (B) in a ratio by weight of A to B of 100: (1–15) as polishing agent.

3. A toothpaste as claimed in claim 2, which contains 1,1'-hexamethylene bis-(4-chlorophenyl)-biguanide (chlorhexidine) in the form of a water-soluble salt as the antimicrobial biguanide.

4. A toothpaste as claimed in claim 3, wherein alkyl glycosides containing 8 to 18 carbon atoms in the alkyl group and having an average degree of oligomerization of the glycoside residue of 1 to 3 are present in a quantity of 0.025 to 2.5% by weight as the alkyl glycosides.

5. A toothpaste as claimed in claim 4, which contains 0.1 to 0.5% by weight of a flavoring oil and 0.1 to 0.7% by weight of a solubilizer from the group consisting of ethoxylated fatty acid glycerides, ethoxylated fatty acid sorbitan partial esters, and fatty acid partial esters of glycerol and sorbitan ethoxylates.

6. A toothpaste as claimed in claim 1, which contains 1,1'-hexamethylene bis-(4-chlorophenyl)-biguanide (chlorhexidine) in the form of a water-soluble salt as the antimicrobial biguanide.

7. A toothpaste as claimed in claim 6, wherein alkyl glycosides containing 8 to 18 carbon atoms in the alkyl group and having an average degree of oligomerization of the glycoside residue of 1 to 3 are present in a quantity of 0.025 to 2.5% by weight as the alkyl glycosides.

8. A toothpaste as claimed in claim 2, wherein alkyl glycosides containing 8 to 18 carbon atoms in the alkyl group and having an average degree of oligomerization of the glycoside residue of 1 to 3 are present in a quantity of 0.025 to 2.5% by weight as the alkyl glycosides.

9. A toothpaste as claimed in claim 1, wherein alkyl glycosides containing 8 to 18 carbon atoms in the alkyl group and having an average degree of oligomerization of the glycoside residue of 1 to 3 are present in a quantity of 0.025 to 2.5% by weight as the alkyl glycosides.

10. A toothpaste as claimed in claim 9, which contains 0.1 to 0.5% by weight of a flavoring oil and 0.1 to 0.7% by weight of a solubilizer from the group consisting of ethoxylated fatty acid glycerides, ethoxylated fatty acid sorbitan partial esters, and fatty acid partial esters of glycerol and sorbitan ethoxylates.

11. A toothpaste as claimed in claim 8, which contains 0.1 to 0.5% by weight of a flavoring oil and 0.1 to 0.7% by weight of a solubilizer from the group consisting of ethoxylated fatty acid glycerides, ethoxylated fatty acid sorbitan partial esters, and fatty acid partial esters of glycerol and sorbitan ethoxylates.

12. A toothpaste as claimed in claim 7, which contains 0.1 to 0.5% by weight of a flavoring oil and 0.1 to 0.7% by weight of a solubilizer from the group consisting of ethoxylated fatty acid glycerides, ethoxylated fatty acid sorbitan partial esters, and fatty acid partial esters of glycerol and sorbitan ethoxylates.

13. A toothpaste as claimed in claim 6, which contains 0.1 to 0.5% by weight of a flavoring oil and 0.1 to 0.7% by weight of a solubilizer from the group consisting of ethoxylated fatty acid glycerides, ethoxylated fatty acid sorbitan partial esters, and fatty acid partial esters of glycerol and sorbitan ethoxylates.

14. A toothpaste as claimed in claim 3, which contains 0.1 to 0.5% by weight of a flavoring oil and 0.1 to 0.7% by weight of a solubilizer from the group consisting of ethoxylated fatty acid glycerides, ethoxylated fatty acid sorbitan partial esters, and fatty acid partial esters of glycerol and sorbitan ethoxylates.

15. A toothpaste as claimed in claim 2, which contains 0.1 to 0.5% by weight of a flavoring oil and 0.1 to 0.7% by weight of a solubilizer from the group consisting of ethoxylated fatty acid glycerides, ethoxylated fatty acid sorbitan partial esters, and fatty acid partial esters of glycerol and sorbitan ethoxylates.

16. A toothpaste as claimed in claim 1, which contains 0.1 to 0.5% by weight of a flavoring oil and 0.1 to 0.7% by weight of a solubilizer from the group consisting of ethoxylated fatty acid glycerides, ethoxylated fatty acid sorbitan partial esters, and fatty acid partial esters of glycerol and sorbitan ethoxylates.

* * * * *